United States Patent
Anderson et al.

(10) Patent No.: US 10,149,664 B2
(45) Date of Patent: *Dec. 11, 2018

(54) LARGE SAMPLE LOW ASPECT RATIO BIOPSY NEEDLE

(75) Inventors: Tyson D. Anderson, Gilbert, AZ (US); Daniel O. Almazan, Peoria, AZ (US); Dnyanesh A. Talpade, Kinnelon, NJ (US)

(73) Assignee: C. R. Bard, Inc., Tempe, AZ (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/585,238

(22) Filed: Aug. 14, 2012

(65) Prior Publication Data

US 2013/0023789 A1    Jan. 24, 2013

Related U.S. Application Data (62) Division of application No. 12/446,664, filed as application No. PCT/US2007/082259 on Oct. 23, 2007, now Pat. No. 8,262,586.

(60) Provisional application No. 60/862,723, filed on Oct. 24, 2006.

(51) Int. Cl.
    *A61B 10/02* (2006.01)
(52) U.S. Cl.
    CPC ...... *A61B 10/0275* (2013.01); *A61B 10/0233* (2013.01); *A61B 10/0283* (2013.01)
(58) Field of Classification Search
    USPC .......................... 600/564–568; 606/170, 171
    See application file for complete search history.

(56) References Cited

U.S. PATENT DOCUMENTS

| | | |
|---|---|---|
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A * | 11/1969 | Griffith ........................ 600/567 |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |

(Continued)

FOREIGN PATENT DOCUMENTS

| | | |
|---|---|---|
| CN | 101011268 A | 8/2007 |
| CN | 101032420 A | 9/2007 |

(Continued)

OTHER PUBLICATIONS

Affix, www.merriam-webster.com/dictionary/affix, printed Feb. 8, 2016, 4 pages.*

(Continued)

*Primary Examiner* — Matthew Kremer (57) ABSTRACT

A high aspect ratio biopsy needle achieves reliable performance with large solid sample size by means of a variety of features and combinations thereof, including support to prevent bending, reinforcement of the needle, and cutting edges arranged to resist deformation.

22 Claims, 5 Drawing Sheets

(56) References Cited

U.S. PATENT DOCUMENTS

| | | | | |
|---|---|---|---|---|
| 3,800,783 | A | 4/1974 | Jamshidi | |
| 3,844,272 | A | 10/1974 | Banko | |
| 3,882,849 | A | 5/1975 | Jamshidi | |
| 3,889,682 | A | 6/1975 | Denis et al. | |
| 3,916,948 | A | 11/1975 | Benjamin | |
| 4,275,730 | A | 6/1981 | Hussein | |
| 4,282,884 | A | 8/1981 | Boebel | |
| 4,306,570 | A | 12/1981 | Matthews | |
| 4,354,092 | A | 10/1982 | Manabe et al. | |
| 4,393,879 | A | 7/1983 | Milgrom | |
| 4,445,509 | A | 5/1984 | Auth | |
| 4,490,137 | A | 12/1984 | Moukheibir | |
| 4,549,554 | A | 10/1985 | Markham | |
| 4,577,629 | A * | 3/1986 | Martinez | 606/171 |
| 4,589,414 | A | 5/1986 | Yoshida et al. | |
| 4,603,694 | A | 8/1986 | Wheeler | |
| 4,605,011 | A | 8/1986 | Naslund | |
| 4,616,215 | A | 10/1986 | Maddalena | |
| 4,617,430 | A | 10/1986 | Bryant | |
| 4,620,539 | A | 11/1986 | Andrews et al. | |
| 4,643,197 | A | 2/1987 | Greene et al. | |
| 4,645,153 | A | 2/1987 | Granzow et al. | |
| 4,678,459 | A | 7/1987 | Onik et al. | |
| 4,696,298 | A | 9/1987 | Higgins et al. | |
| 4,702,260 | A | 10/1987 | Wang | |
| 4,706,687 | A | 11/1987 | Rogers | |
| 4,776,346 | A | 10/1988 | Beraha et al. | |
| 4,792,327 | A | 12/1988 | Swartz | |
| 4,832,044 | A | 5/1989 | Garg | |
| 4,844,064 | A | 7/1989 | Thimsen et al. | |
| 4,844,087 | A | 7/1989 | Garg | |
| 4,850,354 | A | 7/1989 | McGurk-Burleson et al. | |
| 4,893,635 | A | 1/1990 | de Groot et al. | |
| 4,907,598 | A | 3/1990 | Bauer | |
| RE33,258 | E | 7/1990 | Onik et al. | |
| 4,940,061 | A | 7/1990 | Terwilliger et al. | |
| 4,952,817 | A | 8/1990 | Bolan et al. | |
| 4,958,625 | A | 9/1990 | Bates et al. | |
| 4,967,762 | A | 11/1990 | DeVries | |
| 4,986,278 | A | 1/1991 | Ravid et al. | |
| 4,986,279 | A | 1/1991 | O'Neill | |
| 4,986,807 | A | 1/1991 | Farr | |
| 4,989,614 | A | 2/1991 | Dejter, Jr. et al. | |
| 5,025,797 | A | 6/1991 | Baran | |
| 5,048,538 | A | 9/1991 | Terwilliger et al. | |
| 5,057,822 | A | 10/1991 | Hoffman | |
| 5,078,603 | A | 1/1992 | Cohen | |
| 5,125,413 | A | 6/1992 | Baran | |
| 5,138,245 | A | 8/1992 | Mattinger et al. | |
| 5,146,921 | A | 9/1992 | Terwilliger et al. | |
| 5,156,160 | A | 10/1992 | Bennett | |
| 5,158,528 | A | 10/1992 | Walker et al. | |
| 5,172,702 | A | 12/1992 | Leigh et al. | |
| 5,176,628 | A | 1/1993 | Charles et al. | |
| 5,183,052 | A | 2/1993 | Terwilliger | |
| 5,197,484 | A | 3/1993 | Kornberg et al. | |
| 5,211,627 | A * | 5/1993 | William | A61M 25/003 604/523 |
| 5,223,012 | A | 6/1993 | Best et al. | |
| 5,225,763 | A | 7/1993 | Krohn et al. | |
| 5,234,000 | A | 8/1993 | Hakky et al. | |
| 5,236,334 | A | 8/1993 | Bennett | |
| 5,242,404 | A | 9/1993 | Conley et al. | |
| 5,249,583 | A | 10/1993 | Mallaby | |
| 5,254,117 | A * | 10/1993 | Rigby | A61B 18/1482 606/42 |
| 5,282,476 | A | 2/1994 | Terwilliger | |
| 5,282,477 | A | 2/1994 | Bauer | |
| 5,290,253 | A | 3/1994 | Kira | |
| 5,305,762 | A | 4/1994 | Acorn et al. | |
| 5,324,306 | A | 6/1994 | Makower et al. | |
| 5,334,183 | A | 8/1994 | Wuchinich | |
| 5,335,671 | A | 8/1994 | Clement | |
| 5,368,029 | A | 11/1994 | Holcombe et al. | |
| 5,368,045 | A | 11/1994 | Clement et al. | |
| 5,383,874 | A | 1/1995 | Jackson et al. | |
| 5,397,462 | A | 3/1995 | Higashijima et al. | |
| 5,400,798 | A | 3/1995 | Baran | |
| 5,439,474 | A | 8/1995 | Li | |
| 5,458,112 | A | 10/1995 | Weaver | |
| 5,469,860 | A | 11/1995 | DeSantis | |
| 5,471,994 | A | 12/1995 | Guirguis | |
| 5,479,486 | A | 12/1995 | Saji | |
| 5,485,917 | A | 1/1996 | Early | |
| 5,492,130 | A | 2/1996 | Chiou | |
| 5,496,860 | A | 3/1996 | Matsumoto et al. | |
| 5,511,556 | A * | 4/1996 | DeSantis | 600/567 |
| 5,526,822 | A | 6/1996 | Burbank et al. | |
| 5,535,755 | A | 7/1996 | Heske | |
| 5,546,957 | A | 8/1996 | Heske | |
| 5,554,151 | A | 9/1996 | Hinchliffe | |
| 5,560,373 | A * | 10/1996 | De Santis | 600/566 |
| 5,564,436 | A | 10/1996 | Hakky et al. | |
| 5,569,284 | A | 10/1996 | Young et al. | |
| 5,575,293 | A | 11/1996 | Miller et al. | |
| 5,591,170 | A | 1/1997 | Spievack et al. | |
| 5,601,583 | A | 2/1997 | Donahue et al. | |
| 5,601,585 | A | 2/1997 | Banik et al. | |
| 5,602,449 | A | 2/1997 | Krause et al. | |
| 5,612,738 | A | 3/1997 | Kim | |
| 5,617,874 | A | 4/1997 | Baran | |
| 5,649,547 | A | 7/1997 | Ritchart et al. | |
| 5,655,542 | A | 8/1997 | Weilandt | |
| 5,655,657 | A | 8/1997 | Roshdy | |
| 5,665,101 | A | 9/1997 | Becker et al. | |
| 5,669,394 | A | 9/1997 | Bergey et al. | |
| 5,699,909 | A | 12/1997 | Foster | |
| 5,700,265 | A | 12/1997 | Romano | |
| 5,709,697 | A | 1/1998 | Ratcliff et al. | |
| 5,720,760 | A | 2/1998 | Becker et al. | |
| 5,735,264 | A | 4/1998 | Siczek et al. | |
| 5,752,923 | A | 5/1998 | Terwilliger | |
| 5,755,714 | A | 5/1998 | Murphy-Chutorian | |
| 5,766,135 | A | 6/1998 | Terwilliger | |
| 5,769,086 | A | 6/1998 | Ritchart et al. | |
| 5,769,795 | A | 6/1998 | Terwilliger | |
| 5,775,333 | A | 7/1998 | Burbank et al. | |
| 5,779,649 | A | 7/1998 | Herbert | |
| 5,788,651 | A | 8/1998 | Weilandt | |
| 5,792,167 | A | 8/1998 | Kablik et al. | |
| 5,807,282 | A | 9/1998 | Fowler | |
| 5,817,033 | A | 10/1998 | DeSantis et al. | |
| 5,817,034 | A | 10/1998 | Milliman et al. | |
| 5,823,970 | A * | 10/1998 | Terwilliger | 600/564 |
| 5,827,305 | A | 10/1998 | Gordon | |
| 5,830,219 | A | 11/1998 | Bird et al. | |
| D403,405 | S | 12/1998 | Terwilliger | |
| 5,857,982 | A | 1/1999 | Milliman et al. | |
| 5,871,699 | A | 2/1999 | Ruggeri | |
| 5,879,365 | A | 3/1999 | Whitfield et al. | |
| 5,908,233 | A | 6/1999 | Heskett et al. | |
| 5,913,857 | A | 6/1999 | Ritchart et al. | |
| 5,916,198 | A | 6/1999 | Dillow | |
| 5,916,229 | A * | 6/1999 | Evans | 606/171 |
| 5,928,164 | A | 7/1999 | Burbank et al. | |
| 5,944,673 | A | 8/1999 | Gregoire et al. | |
| 5,951,490 | A | 9/1999 | Fowler | |
| 5,951,575 | A | 9/1999 | Bolduc et al. | |
| 5,964,716 | A | 10/1999 | Gregoire et al. | |
| 5,971,939 | A | 10/1999 | DeSantis et al. | |
| 5,976,164 | A | 11/1999 | Bencini et al. | |
| 5,980,469 | A | 11/1999 | Burbank et al. | |
| 5,980,545 | A | 11/1999 | Pacala et al. | |
| 6,007,495 | A | 12/1999 | Matula | |
| 6,007,497 | A | 12/1999 | Huitema | |
| 6,007,556 | A | 12/1999 | Kablik et al. | |
| 6,017,316 | A | 1/2000 | Ritchart et al. | |
| 6,018,227 | A | 1/2000 | Kumar et al. | |
| 6,019,733 | A | 2/2000 | Farascioni | |
| 6,022,324 | A | 2/2000 | Skinner | |
| 6,022,325 | A | 2/2000 | Siczek et al. | |
| 6,027,458 | A | 2/2000 | Janssens | |
| 6,032,673 | A | 3/2000 | Savage et al. | |
| 6,036,657 | A | 3/2000 | Milliman et al. | |

(56) References Cited

U.S. PATENT DOCUMENTS

| | | | |
|---|---|---|---|
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 * | 7/2004 | Miller et al. ............ 600/568 |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Homer et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 * | 1/2009 | Weikel, Jr. ......... A61B 10/0275 600/564 |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,841,991 B2 | 11/2010 | Douglas et al. |
| 7,846,109 B2 | 12/2010 | Parihar et al. |
| 7,854,706 B2 | 12/2010 | Hibner |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,974,681 B2 | 7/2011 | Wallace et al. |
| 8,002,713 B2 | 8/2011 | Heske et al. |
| 8,016,844 B2 | 9/2011 | Privitera et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,671 B2 | 12/2011 | Boulais et al. |
| 8,083,687 B2 | 12/2011 | Parihar |
| 8,109,885 B2 | 2/2012 | Heske et al. |
| 8,118,755 B2 | 2/2012 | Hibner et al. |

(56) References Cited

U.S. PATENT DOCUMENTS

| | | | |
|---|---|---|---|
| 8,172,771 B2 | 3/2012 | Miller et al. | |
| 8,152,738 B2 | 4/2012 | Li et al. | |
| 8,187,204 B2 | 5/2012 | Miller et al. | |
| 8,190,238 B2 | 5/2012 | Moll et al. | |
| 8,206,409 B2 | 6/2012 | Privitera et al. | |
| 8,251,916 B2 | 8/2012 | Speeg et al. | |
| 8,262,586 B2* | 9/2012 | Anderson et al. | 600/567 |
| 8,277,393 B2 | 10/2012 | Miller et al. | |
| 8,287,465 B2 | 10/2012 | Hardin et al. | |
| 8,313,444 B2 | 11/2012 | Thompson et al. | |
| 8,343,069 B2 | 1/2013 | Uchiyama et al. | |
| 8,430,825 B2 | 4/2013 | Mark | |
| 8,430,827 B2 | 4/2013 | Nicoson et al. | |
| 8,956,306 B2 | 2/2015 | Hibner | |
| 2001/0007925 A1 | 7/2001 | Ritchart et al. | |
| 2001/0011156 A1 | 8/2001 | Viola et al. | |
| 2001/0012919 A1 | 8/2001 | Terwilliger | |
| 2001/0014779 A1 | 8/2001 | Burbank et al. | |
| 2001/0034530 A1 | 10/2001 | Malackowski et al. | |
| 2001/0044595 A1 | 11/2001 | Reydel et al. | |
| 2001/0047183 A1 | 11/2001 | Privitera et al. | |
| 2002/0000403 A1 | 1/2002 | Tanaka et al. | |
| 2002/0029007 A1* | 3/2002 | Bryan et al. | 600/565 |
| 2002/0045840 A1 | 4/2002 | Voegele et al. | |
| 2002/0065474 A1 | 5/2002 | Viola | |
| 2002/0067151 A1 | 6/2002 | Tanishita | |
| 2002/0068878 A1* | 6/2002 | Jasonni et al. | 600/566 |
| 2002/0082518 A1 | 6/2002 | Weiss et al. | |
| 2002/0107043 A1 | 8/2002 | Adamson et al. | |
| 2002/0115942 A1 | 8/2002 | Stanford et al. | |
| 2002/0120212 A1 | 8/2002 | Ritchart et al. | |
| 2002/0143269 A1 | 10/2002 | Neuenfeldt | |
| 2002/0151822 A1 | 10/2002 | Burdorff et al. | |
| 2002/0156395 A1 | 10/2002 | Stephens et al. | |
| 2003/0023188 A1 | 1/2003 | Kritzman et al. | |
| 2003/0023239 A1 | 1/2003 | Burbank et al. | |
| 2003/0073929 A1 | 4/2003 | Baltschun et al. | |
| 2003/0093103 A1 | 5/2003 | Malackowski et al. | |
| 2003/0130593 A1 | 7/2003 | Gonzalez | |
| 2003/0130677 A1 | 7/2003 | Whitman et al. | |
| 2003/0163142 A1 | 8/2003 | Paltieli et al. | |
| 2003/0229293 A1 | 12/2003 | Hibner et al. | |
| 2003/0233101 A1 | 12/2003 | Lubock et al. | |
| 2004/0015079 A1 | 1/2004 | Berger et al. | |
| 2004/0019297 A1* | 1/2004 | Angel | 600/564 |
| 2004/0030367 A1 | 2/2004 | Yamaki et al. | |
| 2004/0034280 A1 | 2/2004 | Privitera et al. | |
| 2004/0049128 A1 | 3/2004 | Miller et al. | |
| 2004/0054299 A1 | 3/2004 | Burdorff et al. | |
| 2004/0082915 A1 | 4/2004 | Kadan | |
| 2004/0092980 A1 | 5/2004 | Cesarini et al. | |
| 2004/0092992 A1 | 5/2004 | Adams et al. | |
| 2004/0162505 A1 | 8/2004 | Kaplan et al. | |
| 2004/0167428 A1 | 8/2004 | Quick et al. | |
| 2004/0186393 A1 | 9/2004 | Leigh et al. | |
| 2004/0210161 A1 | 10/2004 | Burdorff et al. | |
| 2004/0215103 A1 | 10/2004 | Mueller, Jr. et al. | |
| 2004/0220495 A1 | 11/2004 | Cahir et al. | |
| 2004/0230135 A1 | 11/2004 | Merkle | |
| 2004/0230188 A1* | 11/2004 | Cioanta | A61B 18/04 606/34 |
| 2004/0249278 A1 | 12/2004 | Krause | |
| 2004/0267157 A1 | 12/2004 | Miller et al. | |
| 2005/0004492 A1 | 1/2005 | Burbank et al. | |
| 2005/0004559 A1 | 1/2005 | Quick et al. | |
| 2005/0010131 A1 | 1/2005 | Burbank et al. | |
| 2005/0020909 A1 | 1/2005 | Moctezuma de la Barrera et al. | |
| 2005/0027210 A1 | 2/2005 | Miller | |
| 2005/0044489 A1 | 3/2005 | Foerster et al. | |
| 2005/0049521 A1 | 3/2005 | Miller et al. | |
| 2005/0054947 A1 | 3/2005 | Goldenberg | |
| 2005/0065453 A1 | 3/2005 | Shabaz et al. | |
| 2005/0080355 A1* | 4/2005 | Mark | A61B 10/0275 600/566 |
| 2005/0085838 A1 | 4/2005 | Thompson et al. | |
| 2005/0088120 A1 | 4/2005 | Avis | |
| 2005/0101879 A1 | 5/2005 | Shidham et al. | |
| 2005/0113715 A1 | 5/2005 | Schwindt et al. | |
| 2005/0113716 A1 | 5/2005 | Mueller, Jr. et al. | |
| 2005/0124914 A1* | 6/2005 | Dicarlo et al. | 600/567 |
| 2005/0124915 A1 | 6/2005 | Eggers et al. | |
| 2005/0165328 A1* | 7/2005 | Heske et al. | 600/566 |
| 2005/0165329 A1 | 7/2005 | Taylor et al. | |
| 2005/0177117 A1 | 8/2005 | Crocker et al. | |
| 2005/0193451 A1 | 9/2005 | Quistgaard et al. | |
| 2005/0203439 A1* | 9/2005 | Heske | A61B 10/0233 600/566 |
| 2005/0209530 A1 | 9/2005 | Pflueger | |
| 2005/0215921 A1 | 9/2005 | Hibner et al. | |
| 2005/0275378 A1 | 12/2005 | Canino et al. | |
| 2005/0277829 A1 | 12/2005 | Tsonton et al. | |
| 2005/0277871 A1 | 12/2005 | Selis | |
| 2005/0288605 A1 | 12/2005 | Pellegrino et al. | |
| 2006/0030784 A1 | 2/2006 | Miller et al. | |
| 2006/0074344 A1 | 4/2006 | Hibner | |
| 2006/0074345 A1 | 4/2006 | Hibner | |
| 2006/0074350 A1 | 4/2006 | Cash | |
| 2006/0113958 A1 | 6/2006 | Lobert et al. | |
| 2006/0116603 A1 | 6/2006 | Shibazaki et al. | |
| 2006/0122535 A1 | 6/2006 | Daum | |
| 2006/0129063 A1 | 6/2006 | Thompson et al. | |
| 2006/0149162 A1 | 7/2006 | Daw et al. | |
| 2006/0178666 A1 | 8/2006 | Cosman et al. | |
| 2006/0184063 A1 | 8/2006 | Miller | |
| 2006/0200042 A1* | 9/2006 | Weikel, Jr. | A61B 10/0275 600/566 |
| 2006/0241515 A1 | 10/2006 | Jones et al. | |
| 2006/0258956 A1 | 11/2006 | Haberstich et al. | |
| 2006/0260994 A1 | 11/2006 | Mark et al. | |
| 2007/0016101 A1 | 1/2007 | Feldman et al. | |
| 2007/0027407 A1 | 2/2007 | Miller | |
| 2007/0032741 A1 | 2/2007 | Hibner et al. | |
| 2007/0032743 A1 | 2/2007 | Hibner | |
| 2007/0055173 A1 | 3/2007 | DeLonzor et al. | |
| 2007/0073326 A1 | 3/2007 | Miller et al. | |
| 2007/0090788 A1 | 4/2007 | Hansford et al. | |
| 2007/0106176 A1* | 5/2007 | Mark | A61B 10/0275 600/566 |
| 2007/0118048 A1 | 5/2007 | Stephens et al. | |
| 2007/0118049 A1 | 5/2007 | Viola | |
| 2007/0123797 A1 | 5/2007 | Krause | |
| 2007/0161925 A1 | 7/2007 | Quick et al. | |
| 2007/0167736 A1 | 7/2007 | Dietz et al. | |
| 2007/0167782 A1 | 7/2007 | Callahan et al. | |
| 2007/0167828 A1 | 7/2007 | Saadat | |
| 2007/0167943 A1 | 7/2007 | Janssen et al. | |
| 2007/0179401 A1 | 8/2007 | Hibner | |
| 2007/0213590 A1 | 9/2007 | Squicciarini | |
| 2007/0213630 A1 | 9/2007 | Beckman et al. | |
| 2007/0213632 A1 | 9/2007 | Okazaki et al. | |
| 2007/0219572 A1 | 9/2007 | Deck et al. | |
| 2007/0236180 A1 | 10/2007 | Rodgers | |
| 2007/0239067 A1 | 10/2007 | Hibner et al. | |
| 2007/0255173 A1 | 11/2007 | Hibner | |
| 2007/0270710 A1 | 11/2007 | Frass et al. | |
| 2007/0276288 A1 | 11/2007 | Khaw | |
| 2007/0287933 A1 | 12/2007 | Phan et al. | |
| 2007/0292858 A1 | 12/2007 | Chen et al. | |
| 2007/0293788 A1 | 12/2007 | Entrekin et al. | |
| 2007/0293830 A1 | 12/2007 | Martin | |
| 2008/0004545 A1 | 1/2008 | Garrison | |
| 2008/0007217 A1 | 1/2008 | Riley | |
| 2008/0015429 A1 | 1/2008 | Tsonton et al. | |
| 2008/0021487 A1 | 1/2008 | Heisler | |
| 2008/0021488 A1 | 1/2008 | Berberich | |
| 2008/0030170 A1 | 2/2008 | Dacquay et al. | |
| 2008/0064925 A1 | 3/2008 | Gill et al. | |
| 2008/0064984 A1 | 3/2008 | Pflueger | |
| 2008/0071193 A1 | 3/2008 | Reuber et al. | |
| 2008/0079391 A1 | 4/2008 | Schroeck et al. | |
| 2008/0103411 A1 | 5/2008 | Van Bladel et al. | |
| 2008/0110261 A1 | 5/2008 | Randall et al. | |
| 2008/0125634 A1 | 5/2008 | Ryan et al. | |
| 2008/0135443 A1 | 6/2008 | Frojd et al. | |

(56) References Cited

U.S. PATENT DOCUMENTS

| | | |
|---|---|---|
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0171242 A1 | 7/2009 | Hibner |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0160823 A1 | 6/2010 | Parihar et al. |
| 2010/0210966 A1 | 8/2010 | Videbaek |
| 2010/0222700 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0324449 A1 | 12/2010 | Rostaing et al. |
| 2011/0004119 A1 | 1/2011 | Hoffa et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | McCullough et al. |
| 2011/0224577 A1 | 9/2011 | Park |
| 2011/0295150 A1 | 12/2011 | McCullough et al. |
| 2012/0071787 A1 | 3/2012 | Reuber et al. |
| 2012/0095366 A1 | 4/2012 | Heske et al. |
| 2012/0130275 A1 | 5/2012 | Chudzik et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023791 A1 | 1/2013 | Thompson et al. |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0025415 A1 | 1/2015 | Videbaek et al. |
| 2015/0073301 A1 | 3/2015 | Videbaek et al. |
| 2015/0094613 A1 | 4/2015 | Jorgensen et al. |
| 2015/0133814 A1 | 5/2015 | Almazan |
| 2015/0148702 A1 | 5/2015 | Heske et al. |
| 2015/0190124 A1 | 7/2015 | Mccullough et al. |
| 2015/0238174 A1 | 8/2015 | Reuber et al. |
| 2015/0342579 A1 | 12/2015 | Heske et al. |
| 2016/0256138 A1 | 9/2016 | Videbaek et al. |
| 2016/0367229 A1 | 12/2016 | Jorgensen et al. |
| 2016/0374650 A1 | 12/2016 | Heske et al. |
| 2017/0042517 A1 | 2/2017 | Heske et al. |
| 2017/0181732 A1 | 6/2017 | Videbaek et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |

(56) References Cited

FOREIGN PATENT DOCUMENTS

| | | |
|---|---|---|
| WO | 2008131362 A2 | 10/2008 |
| WO | 2011019343 A1 | 2/2011 |

OTHER PUBLICATIONS

Definition of Channel by Merriam-Webster, www.merriam-webster.com/dictionary/channel, printed Jan. 4, 2017 (15 pages).*
Definition of Therethrough by Merriam-Webster, www.merriam-webster.com/dictionary/therethrough, printed Jan. 4, 2017 (10 pages).*
"Elongate", www.merriam-webster.com/dictionary/elongate, printed out on Dec. 5, 2017, 13 pages.*

* cited by examiner

Fig. 9

LARGE SAMPLE LOW ASPECT RATIO BIOPSY NEEDLE

PRIORITY CLAIM AND INCORPORATION BY REFERENCE

This application is a division of U.S. patent application Ser. No. 12/446,664 filed Apr. 22, 2009, now U.S. Pat. No. 8,262,586, which is a U.S. national phase of International Application No. PCT/US2007/082259, filed Oct. 23, 2007, which claims priority to U.S. Provisional Application Serial No. 60/862,723, filed Oct. 24, 2006, which is hereby incorporated by reference in its entirety.

TECHNICAL FIELD

The present invention relates to biopsy needles and more particularly to small-diameter biopsy needles suited for automated sampling operation.

BACKGROUND ART

Often, it is either desirable or necessary to obtain specimens of tissue from humans and other animals, particularly in the diagnosis and treatment of patients with cancerous tumors, premalignant conditions, and other diseases or disorders. For example, when it is discovered that suspicious conditions exist, either by means of x-ray or ultrasound imaging in various tissues of the body, a physician typically performs a biopsy to determine if the cells at the suspected site are cancerous.

A biopsy can be done either by an open or percutaneous technique. Open biopsy is an invasive procedure using a scalpel, whereby either a portion (incisional biopsy) or the entire mass (excisional biopsy) is removed. Percutaneous biopsy is usually done with a needle-like instrument through a relatively small incision, and can be performed by fine needle aspiration (FNA) or through the taking of a core biopsy sample. In FNA biopsy, individual cells or clusters of cells are obtained for cytologic examination and can be prepared such as in a Papanicolaou smear. In a core biopsy, a core or fragment of the tissue is obtained for histologic examination.

Intact tissue from the organ, lesion, or tumor is preferred by medical personnel in order to arrive at a definitive diagnosis regarding the patient's condition. In most cases only part of the tissue in question needs to be sampled. The portions of tissue extracted must be indicative of the organ, lesion, or tumor as a whole. Often, multiple tissue samples from various locations of the mass being sampled may be taken.

The percutaneous biopsy procedure can be performed utilizing various techniques and devices. An example is a method and a device that employs a biopsy needle for cutting tissue sample as described in British Patent Publication No. GB 2018601A. In the described biopsy device, living tissue is drawn into a cutting region under vacuum. The vacuum is created in the needle by employing connecting lines to a vacuum generator situated outside of a hand piece that holds the cannula. The cutting of the sample is done using a cutting mechanism that moves axially over the cannula. After the needle is withdrawn from the host, the sample is flushed out from the tip of the needle. The vacuum established in the hollow needle is regulated externally from the hand-piece.

Another biopsy mechanism is described in European Patent Publication No. EP 0890 339 A1. A biopsy needle, with a cutting mechanism, is integrated into a hand piece. The needle is connected via connection lines to an external vacuum generator and controls. The cutting device is moveable axially in the hollow space of the biopsy needle. A rotary movement, combined with a manual lengthwise push causes the cutting device to sample the tissue from the host. The sample is transported in the hollow channel of the needle. A similar arrangement is also shown by U.S. Pat. No. 5,526,822.

A vacuum-assisted biopsy device is described in U.S. Patent Publication No. 2001/0011156 A1, provides for a compactly configured hand device, in whose housing all drive elements necessary for propelling the needle of the biopsy needle arrangement are provided. A partial vacuum source is provided separate from the hand device, which can be connected via an appropriate supply line to the needle arrangement inside the hand device at a suitable connection location.

US Patent Publication No. 20050203439, describes a biopsy device for taking tissue samples, which includes a housing, a removable element and a control panel. The removable part has a vacuum pump in the form of a syringe which is driven by a first motor and a biopsy needle which is driven by a separate motor under the control of a controller built into a permanent hand set. The needle and syringe are provided as a sterile package unit.

Small diameter biopsy needles are desirable because they have the potential to generate less tissue trauma in the host during use. Generally, biopsy needles use a cutting tip that slices tissue as the needle is advanced. Since biopsy needles need to be inserted a considerable distance before reaching the location of the tissue to be sampled, having a small diameter means less tissue is cut by the cutting tip.

It would be desirable for a biopsy needle of small diameter to provide greater sample size with less trauma than larger size needles. But small-diameter needles are believed to pose a greater design challenge because of the structural demands on a small diameter device.

DISCLOSURE OF INVENTION

A biopsy needle must endure significant loads, which makes it difficult to create biopsy needles with small diameters. If, for example, a 10 gauge needle is simply scaled down in size, every dimension, including wall thickness, length, the size of the sample recess, and the gaps between the stylet and the sheath, is reduced. If tolerances are not scaled, the gaps remain constant which means the stylet has to be reduced by a disproportionate amount in order to reduce the outside needle diameter. As a result, bending forces which are of little concern in a 10 gauge needle, are significant in a 14 gauge needle. In addition, the wall of the sample basket, which, reduced in thickness, must withstand the shearing forces caused by drawing tissue under vacuum into the sample recess. Typically, the constraints force design concessions. For example most 14 gauge needles are able to dissect samples that are only a tenth as large as a 10 gauge needle.

Although the following is not a comprehensive list of features, three major features the invention address the above problems permitting a reliable 14 gauge needle with large sample size. First, longitudinal cutting edges on the sides of the sample recess are located at a greater radial distance from the axis of the stylet than the inner diameter of the sample recess. This improves the ability of the walls of the sample recess to withstand shearing forces resulting from drawing tissue under vacuum into the sample recess.

Second, the stylet is reinforced by an internal longitudinal reinforcement element, preferably along the entire length of the stylet proximal of the sample recess. Preferably, the reinforcement is affixed to the stylet, for example by welding. Third, the proximal end, along a substantial length thereof, is supported and constrained to resist bending thereof.

According to an embodiment, a biopsy device has a generally cylindrical hollow stylet having a uniform wall thickness. The stylet has an inner diameter, an outer diameter, and a longitudinal axis. The stylet has a distal end, and a proximal end, the distal and proximal ends being disposed on the axis. The stylet has a working length from the distal end that extends beyond a housing when inserted therein. A longitudinal recess forms a sample chamber that is positioned adjacent the distal end extending axially a distance of between 10 and 25% of the working length. More preferably, the sample chamber extends axially a distance of about 0.75 inch. A longitudinal insert is connected to the stylet such that additional bending-resisting reinforcement is provided to the stylet.

Preferably, the longitudinal insert is affixed within the stylet along a major fraction of the working length and more preferably, the longitudinal insert is affixed along most of the working length. Preferably, the longitudinal insert is a cylinder. The cylinder preferably has a lumen whose diameter is approximately 0.0025 in. The longitudinal insert is preferably affixed between the recess and a position proximal of the distal end. The stylet's ratio of wall diameter to the wall thickness is preferably less than 15 and more preferably about 10. Note that although other configurations of reinforcement inserts may be used, which have one or more channels or lumens, preferably, no single open area facing the sample chamber is greater than about 0.0025 in. equivalent diameter to prevent solid sample material being drawn into the one or more channels. Equivalent diameter is four times the open area divided by the internal perimeter of the open area.

According to another embodiment, a biopsy device has a generally cylindrical hollow stylet having a distal end with a sample recess configured to receive biopsy samples, and a proximal portion. A mounting member is configured to support the proximal portion of the stylet such that bending of the proximal portion is resisted by the mounting member supporting the proximal portion at at least three support points therealong. A longitudinal reinforcement is affixed at multiple affixation points to the stylet and extending along a major fraction of the stylet and also extending between the at least three support points, such that the reinforcement also resists bending. Preferably, the at least three support points are included in a continuous series of points of contact between a longitudinal reinforcement and the mounting member. Preferably, the stylet has a working length from the distal end that extends axially of the mounting member when held thereby. Preferably, the sample recess has cutting edges extending parallel to an axis joining the distal end and the proximal portion, the cutting edges being on lateral sides of the longitudinal recess. Preferably, the cutting edges define an apex angle of about 40°.

According to another embodiment, a biopsy device has a generally cylindrical hollow stylet having a uniform wall thickness, an inner diameter, an outer diameter, and a longitudinal axis. The stylet preferably has a distal end with a sample recess configured to receive biopsy samples. The stylet also has a proximal end, the distal and proximal ends being disposed on the axis. Preferably, a mounting structure holds the stylet, the stylet having a working length from the distal end that extends distally of the mounting structure when supported thereby. The longitudinal recess forms a sample chamber and positioned adjacent the distal end extending axially a distance of between 10 and 25% of the working length. The longitudinal recess preferably has cutting edges extending parallel to the axis on lateral sides of the longitudinal recess. The cutting edges preferably have a depth, perpendicular to the axis, of between 2.5 and 4 times the wall thickness. The distance between the cutting edges is preferably less than the outer diameter and greater than the inner diameter.

A longitudinal insert may also be included to provide additional reinforcement to the stylet. The longitudinal insert is preferably affixed within the stylet along a major fraction of the working length. The longitudinal insert is preferably affixed between the recess and a position distal of the proximal end. The ratio of the diameter to the wall thickness is preferably less than 15 and, more preferably, about 10.

According to another embodiment, a biopsy device has a generally cylindrical hollow stylet having a uniform wall thickness, an inner diameter, an outer diameter, and a longitudinal axis. The stylet has a distal end with a sample recess configured to receive biopsy samples, and a proximal end, the distal and proximal ends being disposed on the axis. A mounting structure holds the stylet, the stylet having a working length from the distal end that extends distally of the mounting structure when supported thereby. A longitudinal recess forms a sample chamber and positioned adjacent the distal end extending axially a distance of between 10 and 25% of the working length. A longitudinal insert is connected to the stylet such that additional bending-resisting reinforcement is provided to the stylet. The longitudinal insert is affixed within the stylet along a major fraction of the working length. The longitudinal insert may be a cylinder. The cylinder has a lumen whose diameter is approximately 0.0025 in. The longitudinal insert is affixed within the stylet along a major fraction of the working length.

According to another embodiment, a biopsy device has a generally cylindrical hollow stylet having a uniform wall thickness, an inner diameter, an outer diameter, and a longitudinal axis. The stylet has a distal end with a sample recess configured to receive biopsy samples, and a proximal end, the distal and proximal ends being disposed on the axis. A mounting structure holds the stylet, the stylet having a working length from the distal end that extends distally of the mounting structure when supported thereby. A longitudinal recess forms a sample chamber positioned adjacent the distal end extending axially along a portion of the stylet. A cylindrical longitudinal insert is connected to the stylet such that additional bending-resisting reinforcement is provided to the stylet along a major fraction of its length. Preferably, the cylinder has a lumen whose diameter is no more than 0.0025 in. and preferably about 0.0025 in. The reinforcement is preferably affixed within the stylet along a major fraction of the working length. The reinforcement is affixed between the recess and a position distal of the proximal end. The ratio of the diameter to the wall thickness is about 10.

According to another embodiment, a biopsy device has a generally cylindrical hollow stylet having a uniform wall thickness, an inner diameter, an outer diameter, and a longitudinal axis. The stylet has a distal end with a sample recess configured to receive biopsy samples and a proximal end, the distal and proximal ends being disposed on the axis. A mounting structure holds the stylet, the stylet having a working length from the distal end that extends distally of the mounting structure when supported thereby. A longitudinal recess forms a sample chamber positioned adjacent the distal end extending axially a distance of between 10 and 25% of the working length.

Preferably, the longitudinal recess has cutting edges extending parallel to the axis on lateral sides of the longitudinal recess. The cutting edges have planar faces that lie opposite each other on either side of the axis and define an angle such that the planar faces have a widest spacing at the cutting edge and taper toward the bases of the cutting edges where they widen to the wall thickness of the stylet. The distance between the cutting edges is less than the outer diameter and greater than the inner diameter. Preferably, a longitudinal insert provides additional reinforcement to the stylet. Preferably, the longitudinal insert is affixed within the stylet along a substantial fraction of the working length. Preferably, the longitudinal insert is affixed within the stylet along a most of the working length. Preferably, the longitudinal insert is affixed between the recess and a position distal of the proximal end. Preferably, the ratio of the diameter to the wall thickness is less than 15. More preferably, the ratio of the diameter to the wall thickness is about 10.

According to another embodiment, a biopsy device has a generally cylindrical hollow stylet having a uniform wall thickness, an inner diameter, an outer diameter, and a longitudinal axis. The stylet has a distal end with a sample recess configured to receive biopsy samples and a proximal end, the distal and proximal ends being disposed on the axis. A mounting structure holds the stylet, the stylet having a working length from the distal end that extends distally of the mounting structure when supported thereby. The longitudinal recess has cutting edges extending parallel to the axis on lateral sides of the longitudinal recess. The cutting edges define an apex angle of about 40°.

Preferably, the distance between the cutting edges is less than the outer diameter and greater than the inner diameter. Preferably, a longitudinal insert provides additional reinforcement to the stylet. Preferably, the longitudinal insert is affixed within the stylet along a substantial fraction of the working length. More preferably, the longitudinal insert is affixed within the stylet along a most of the working length. Preferably, the longitudinal insert is affixed between the recess and a position distal of the proximal end. Preferably, the ratio of the diameter to the wall thickness is less than 15. Preferably, the ratio of the diameter to the wall thickness is about 10. Preferably, the cutting edges having a depth, perpendicular to the axis, of between 2.5 and 4 times the wall thickness.

According to another embodiment, a biopsy device has a generally cylindrical hollow stylet having a distal end with a sample recess configured to receive biopsy samples, and a proximal end, the distal and proximal ends being disposed on an axis. A mounting structure is configured to support a proximal portion of the stylet such that bending of the proximal portion is resisted by supporting the proximal portion at multiple points along the proximal portion.

Preferably, the multiple points are a continuous series of points of contact between an axially-elongated support element within the mounting structure. Preferably, the axially-elongated support element is located at a distal end of the mounting structure. Preferably, the stylet has a working length from the distal end that extends distally of the mounting structure when supported thereby. Preferably, the longitudinal recess has cutting edges extending parallel to the axis on lateral sides of the longitudinal recess. Preferably, the cutting edges define an apex angle of about 40°.

Preferably, the distance between the cutting edges is less than the outer diameter and greater than the inner diameter. Preferably, a longitudinal insert providing additional reinforcement to the stylet. Preferably, the longitudinal insert is affixed within the stylet along a major fraction of the working length. Preferably, the longitudinal insert is affixed within the stylet along a most of the working length. Preferably, the longitudinal insert is affixed between the recess and a position distal of the proximal end. Preferably, the ratio of the diameter to the wall thickness is less than 15. More preferably, the ratio of the diameter to the wall thickness is about 10.

Preferably, the cutting edges having a depth, perpendicular to the axis, of between 2.5 and 4 times the wall thickness. Preferably, a vacuum pump is provided that is capable of drawing a vacuum of at least 21 in. Hg in the stylet. Preferably, the vacuum pump is capable of drawing a vacuum of at least 21 in. Hg in the sample recess.

According to another embodiment, a biopsy device has a generally cylindrical hollow stylet having a distal end with a sample recess configured to receive biopsy samples, a proximal end, the distal and proximal ends being disposed on an axis. A reinforcement element is affixed inside the stylet and located proximal of the sample recess, having at least one channel therethrough, the at least one channel having no single open area adjacent to the sample recess greater than about 0.0025 in. equivalent diameter. A mounting structure is preferably configured to support a proximal portion of the stylet such that bending of the proximal portion is resisted by supporting the proximal portion at multiple points along the proximal portion, at least several of the multiple points being supported at longitudinal locations that coincide with the reinforcement element.

According to another embodiment, a biopsy device has a 14 gauge needle having a generally cylindrical hollow stylet. The stylet has a distal end with a sample recess configured to receive biopsy samples. The sample recess has longitudinal cutting edges on lateral sides thereof, the cutting edges cutting the stylet at about 70% of the stylet outer diameter. Preferably, the cutting edges have internal faces that are angled such that the cutting edges are further apart at their apexes than at their bases.

According to another embodiment a biopsy device has a generally cylindrical hollow stylet having a distal end with a sample recess configured to receive biopsy samples, and a proximal portion. A mounting member is configured to support the proximal portion of the stylet such that bending of the proximal portion is resisted by the mounting member supporting the proximal portion at at least three support points therealong. A longitudinal reinforcement is affixed at multiple affixation points to the stylet and extending along a significant fraction of the stylet and also extending between the at least three support points, such that the reinforcement also resists bending.

According to an embodiment, a biopsy device has a generally cylindrical hollow stylet having a uniform wall thickness. The stylet has an inner diameter, an outer diameter, and a longitudinal axis. The stylet has a distal end, and a proximal end, the distal and proximal ends being disposed on the axis. The stylet has a working length from the distal end that extends beyond a housing when inserted therein. A longitudinal recess forms a sample chamber that extends axially along the working length. A cylindrical longitudinal insert is connected to the stylet such that additional bending-resisting reinforcement is provided to the stylet.

Preferably, the longitudinal insert is affixed within the stylet along a significant fraction of the working length and more preferably, the longitudinal insert is affixed along most of the working length. The insert, in the cylinder embodiment, has a lumen whose diameter is approximately 0.0025 in. The longitudinal insert is preferably affixed between the recess and a position distal of the proximal end. The stylet's ratio of wall diameter to the wall thickness is preferably less than 15 and greater than 4. More preferably, it is in the range of 9-12 and even more preferably, the ratio of the diameter to the wall thickness is about 10 for a stylet whose outer diameter is about 2 mm or a 14 gauge biopsy needle.

According to another embodiment, a biopsy device has a generally cylindrical hollow stylet having a uniform wall thickness. The stylet has an inner diameter, an outer diameter, and a longitudinal axis. The stylet has a distal end, and a proximal end, the distal and proximal ends being disposed on the axis. The stylet has a working length from the distal end that extends beyond a housing when inserted therein. The working length is defined by a distal-most support element attached to the stylet or a position where the stylet is supported along its length when inserted in a housing. A longitudinal recess forms a sample chamber that is positioned adjacent the distal end extending axially a distance of between 10 and 25% of the working length. The longitudinal recess has cutting edges extending parallel to the axis on lateral sides of the longitudinal recess. The cutting edges having planar faces that lie opposite each other on either side of the axis and define an angle such that the planar faces have a widest spacing at the cutting edge. The distance between the cutting edges is less than the outer diameter and greater than the inner diameter.

Preferably, the biopsy device also has a longitudinal insert providing additional reinforcement to the stylet. The longitudinal insert is preferably affixed within the stylet to multiple points separated by a significant fraction of the working length and more preferably, at the ends of the longitudinal insert. The means of affixation may be welding, adhesion, or any other bonding method. The insert may be compression-fitted by heating and subsequent cooling so that it is affixed along its entire length. The longitudinal insert is preferably affixed between the recess and a position distal of the proximal end. The ratio of wall diameter to the wall thickness is preferably less than 15. The ratio of the diameter to the wall thickness is more preferably about 10.

According to yet another embodiment, the biopsy device has a generally cylindrical hollow stylet having an axis, and a distal end with a sample recess configured to receive biopsy samples. At least one support fixture holds the stylet, the fixture having at least first and second support portions separated along the axis of the stylet. The stylet has a proximal portion extending from a point proximal of the sample recess to the first and second support portions. The proximal portion has a stiffness that is substantially greater than a tube whose diameter and wall thickness is the same as the diameter and wall thickness of the sample recess. Preferably, the support fixture has at least a third support portion to prevent bending of the stylet.

According to another embodiment, a biopsy device has a generally cylindrical hollow stylet with a uniform wall thickness, an inner diameter, and an outer diameter. The stylet also has a longitudinal axis and distal and proximal ends. The distal and proximal ends are disposed on the axis. The housing is configured to support a proximal portion of the stylet therewithin such that bending of the proximal portion is resisted by supporting the proximal portion at multiple points along the proximal portion.

According to another embodiment a biopsy device has a generally cylindrical hollow stylet with a uniform wall thickness, an inner diameter, an outer diameter, and a longitudinal axis. The stylet has a distal end and a proximal end. The distal and proximal ends are disposed on the axis. The stylet has a working length from the distal end that extends beyond a housing when inserted therein. The stylet has a longitudinal recess with cutting edges extending parallel to the axis on lateral sides of the longitudinal recess, with the cutting edges defining an apex angle of about 40°.

According to another embodiment, a biopsy device has a generally cylindrical hollow stylet having a distal end with a sample recess configured to receive biopsy samples, and a proximal portion. A mounting member is configured to support the proximal portion of the stylet such that bending of the proximal portion is resisted by the mounting member supporting the proximal portion at at least three support points therealong. The at least three support points may be included in a continuous series of points of contact between a longitudinal reinforcement and the mounting member.

A longitudinal reinforcement may be affixed at multiple affixation points to the stylet and extending along a substantial fraction of the stylet and also extending between the at least three support points, such that the reinforcement also resists bending.

The stylet can have a working length from the distal end that extends axially of the mounting member when held thereby. The sample recess preferably has cutting edges extending parallel to an axis joining the distal end and the proximal portion, the cutting edges being on lateral sides of the longitudinal recess. The cutting edges preferably define an apex angle of about 40°.

According to another embodiment, a biopsy device has a generally stylet having a distal end with a sample recess configured to receive biopsy samples, and a proximal portion. A mounting member is configured to support the proximal portion of the stylet such that bending of the proximal portion is resisted by the mounting member supporting the proximal portion at at least three support points therealong. The proximal portion extends from a point proximal of the sample recess continuous to and between the at least three support points, the proximal portion having a stiffness substantially greater than a portion distal thereto. The proximal portion has a lumen extending to the sample recess. The proximal portion is a cylinder with a lumen therein, the lumen having a substantially smaller equivalent diameter than the sample recess.

MODE(S) FOR CARRYING OUT THE INVENTION

Various driving mechanisms for biopsy needles are known and many are suitable for use with the invention disclosed below. A preferred type of drive mechanism is a self-contained unit disclosed in U.S. patent application Ser. No. 10/500,522, published as U.S. 2005/0203439 (referred to in the background section) filed in the U.S. on Apr. 6, 2005, now U.S. Pat. No. 8,109,885, and U.S. patent application Ser. No. 10/500,518, published as U.S. 2005/0165328, filed in the U.S. on Mar. 1, 2005 (now U.S. Pat. No. 8,002,713), both of which are hereby incorporated by reference as if fully set forth herein.

Referring to FIGS. 1 to 7, a biopsy needle stylet 100 has a sample chamber opening 113 with sloping edges 107 and 109 and sides defined by an internal surface 103 of the stylet 100. The biopsy needle stylet 100 has a fully circular cross-section over most of its length except along the sample chamber opening 113 whose interior surface is indicated at 103. Along the sample chamber opening 113, the stylet 100 has an approximately semicircular cross-section as shown at 100A.

Figure 1A:
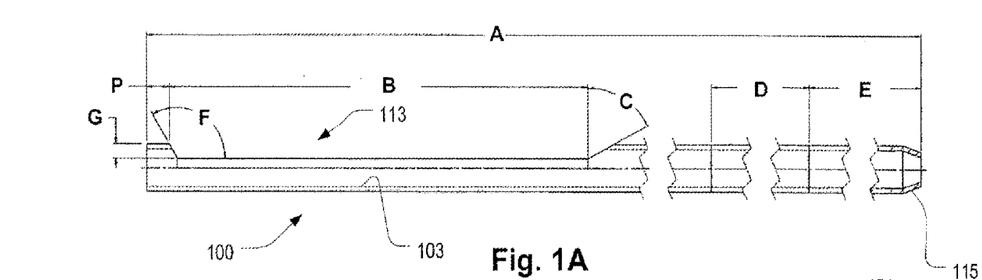
FIG. 1A is a partial section view of a biopsy needle stylet with a sample chamber.
Figures 1B, 2A, 2B, 3:
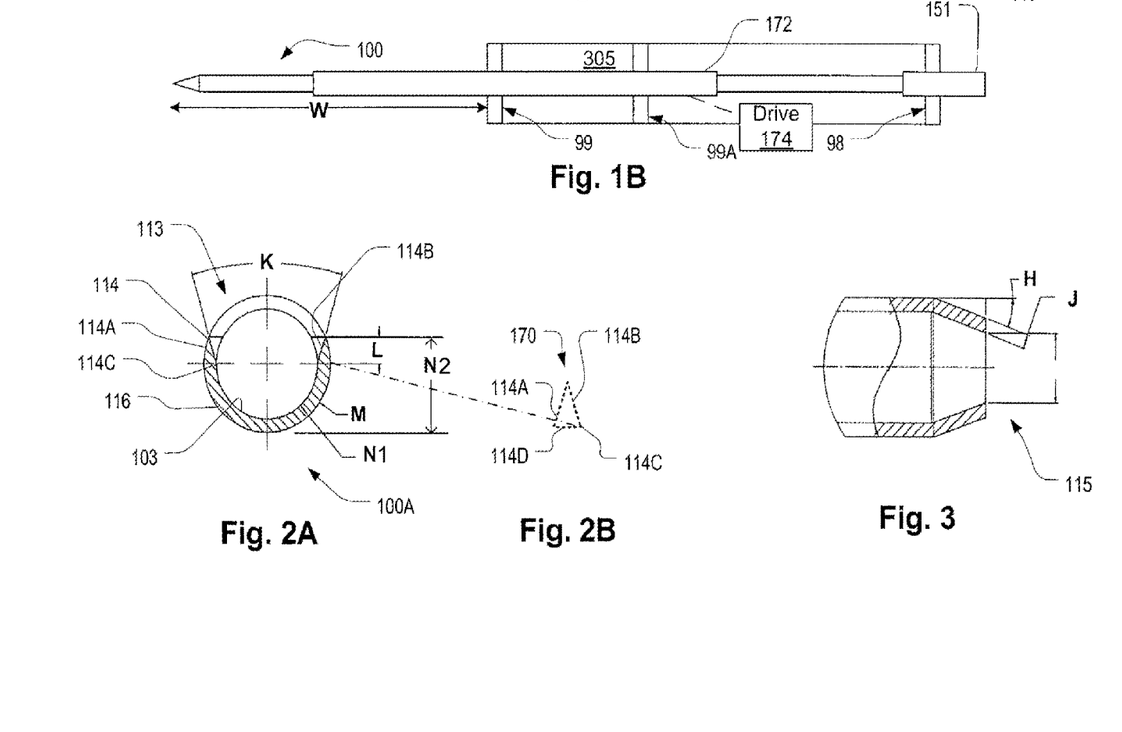
FIG. 1B is a side view of a biopsy needle showing support points.
FIGS. 2A and 2B illustrate a section view of the sample chamber of FIG. 1 and features thereof.
FIG. 3 illustrates a detail taken at a proximal end of the stylet of FIG. 1.

The edges of the sample chamber opening 113 are chamfered to form cutting edges 114 on either side of the sample chamber opening 113. The outsides 114A of the cutting edges 114 are defined by the cylindrical surface 116 of the stylet 100 whereas the inside surfaces 114B of the cutting edges 114 are defined by flat surfaces, also indicated at 114B. The flat surfaces 114B can be created by machining, for example.

The ratios and dimensions discussed below and elsewhere in the present application are preferable for a 14 gauge stylet 100, which preferably includes a cutting sheath as described below. Preferably, the sample chamber opening 113 has a width that is between the outer diameter M of the stylet 100 and the inner diameter N1 of the stylet 100. In addition, preferably, the inside surfaces 114B of the cutting edges 114 slope away from a plane of symmetry 114D such that they are wider apart at the cutting edges 114 than the lines 114C where the inside surfaces 114B of the cutting edges 114 meet the inside surface 103 of the stylet 100.

Note that the inside surfaces 114B of the cutting edges 114 can be flat or curved to achieve substantially the same configuration. Preferably, the distance between the lines 114C, on opposite sides of the inside surface 103 of the stylet, are separated by a distance approximately equal to the inside diameter N1 of the stylet. Preferably, the angle K is greater than 10 degrees and more preferably it is greater than 15° and even more preferably, it is about 19 degrees. Preferably the cutting edges 114 have a height L that is between 2.5 and 4 times the wall thickness J (or M-N1) of the stylet 100. Preferably, in the embodiments of FIGS. 1-7, the ratio of wall thickness J to outer diameter M is between less than 15 and greater than 4. More preferably the ratio of wall thickness J to outer diameter M is about 10. By providing the angle K and the cutting edges 114 at the heights indicated, the nominal apex angle of the cutting angle can be about 40°, which is a desirable angle for cutting edge 114 integrity and sharpness and also for allowing it to withstand the forces generated by a vacuum which pulls tissue into the sample chamber 313 despite relatively thin walls.

The cutting edges 114 lie over the centers of the stylet 100 walls and are not aligned with the inner surface 103. That is, it will be observed that each of the cutting edges 114 lies between inner surface 103 and the outer cylindrical surface 116. In this particular example, it will be observed that the sloping side 114B, the surface 114A and the horizontal line intersecting the line 114C form, approximately, a symmetrical triangle 170. Preferably, the cutting edge 114 lies at a radial distance from the longitudinal axis that is less than the inner radius of the basket inner surface 103. In the example, the cutting edge lies well over the base 114D (the base coinciding with a diametric line as in the illustrations) of the triangle 170 so that the angle K is a substantial angle, i.e., is well above zero. As noted, since the walls are thin, and preferably, as discussed below, vacuum levels relatively high, the forces on the cutting edges can be substantial. The forces are compensated by a force with a component directed toward the center of the stylet so the blade edges 114 tend to be pulled together. Thus, providing the cutting edges with the illustrated shape, with the substantial slope ensured by providing a nonzero, positive angle K, helps to supply this compensating force with less risk of bending. Also, the height N2 of the cutting edges, which is low to help to reduce these forces but not overly so, helps ensure large sample size. In the preferred embodiment, the ratio of the height N2 to outer diameter of the stylet is about 70% (i.e., N2 divided by the diameter of inner surface 103 is about 0.7). Another way of stating this is that the plane defined by the two parallel cutting edges cuts the stylet longitudinally at about 70% of its diameter.

Note that the cutting edge 114 can have multiple angles at the apex and the foregoing is an average at the approach to the apex.

The ratio of the length B of the sample chamber opening 113 to working length (W, defined, according to convention, as the length of the stylet 100 extending beyond the apparatus used to handle the needle, such as a hand-held driver unitary device—not shown—as disclosed in US Patent Publication No. 20050203439) is in the range of 0.10 to 0.25 and more preferably, the ratio is about 0.1 to 0.2. Preferably, the axial length of the sample recess is between 0.7 and 1 inch and more preferably, about 0.75 inches. Referring in particular to FIG. 1B, a needle, including stylet 100 and cutting sheath 172, is provided with first and second support elements 98 and 99. However, the supports may be parts of a handheld or machine-held biopsy device. The working length W is the portion of the stylet 100 extending beyond the most distal support and outside the housing (not shown in FIG. 1B). As discussed further below, additional bend-resisting support is preferably provided as indicated at 99A.

In terms of absolute dimensions, the stylet 100 wall thickness J is preferably between 0.005 in. and 0.007 in. and preferably it is about 0.006 in. Preferably the working length is between about 3.5 and 6.5 inches and more preferably, 5.5 inches. This may be varied depending on particular details of the application. For example, for stereotactic applications, the working length is preferably about 140 mm and for handheld applications, the working length can be as low as about 90 mm Angle C is preferably, between 60 and 65 degrees and 120 degrees and angle F is preferably about 120 degrees. A proximal end 120 of the stylet 100 has a taper forming an angle H of approximately 20 degrees. The total length A of the stylet 100 may be chosen based on the connected driver. In a representative embodiment, the total length A of the stylet 100 is about 10 in.

Stresses on 14 gauge biopsy needles (the gauge specification being based on the diameter of the stylet 100, not the stylet with an overlying cutting sheath, to be describe further on) are high, due to the small diameter. This can make ensuring the smooth and reliable operation of the needle difficult. For example, a longitudinally-advancing cutting sleeve (See for example, U.S. Pat. No. 7,025,732, hereby incorporated by reference as if fully set forth herein), turning around the stylet 100, may warp the stylet 100 or any bending attending normal manual or machine-held use may cause jamming Various means of addressing these issues are discussed herein, including preventing bending and reinforcing the stylet, but it has also proved useful to provide a lubricant between the stylet and the cutting sheath. Preferably, such a lubricant is sterile and biocompatible. Many lubricants are known, for example, mineral oil, silicone, or Hyaluronan-based lubricants may be used. Preferably, a lubricant is provided as part of a sterile-prepackaged disposable biopsy needle consumable unit.

Another preferred mechanism for helping to ensure reliable and smooth operation of a thin needle is to employ a reinforcement in the needle. Preferably this is done without compromising the sample size such as by providing at least one reinforcement element over most of the length of the stylet 100 but not including the sample chamber 113 such that any reinforcement does not reduce the size of the sample chamber 113. In a preferred configuration, the stylet 100 is provided with an insert 127 along a portion of the stylet 100 that is proximal of the sample chamber 113. The insert 127 may take the form of an annular cylindrical tube (also indicated at 127). The insert 127 may be affixed to the stylet 100 with adhesive, by welding, by compression fit, or by nesting. Preferably, the affixation of the reinforcement is affixed at at least two points that are separated by a substantial axial distance. Preferably the insert 127 has a relatively narrow tubular lumen 105 or other channel to allow fluids to be conveyed to and from the sample chamber 113, such as air (vacuum) and saline (for flushing samples out of the chamber 113). The distal end of the insert 127 may have a beveled surface 107 that coincides with the chamfered end of the sample chamber 113. Preferably, the insert 127 runs along most of the length of the stylet 100. The insert 127 preferably has an internal diameter of 0.025 or less, at least at the distal end thereof to act as a tissue block, preventing tissue from being drawn into the lumen 105 when the sample chamber is subjected to a vacuum by drawing fluid through the lumen 105.

Figures 4, 5A, 5B, 6, 7:
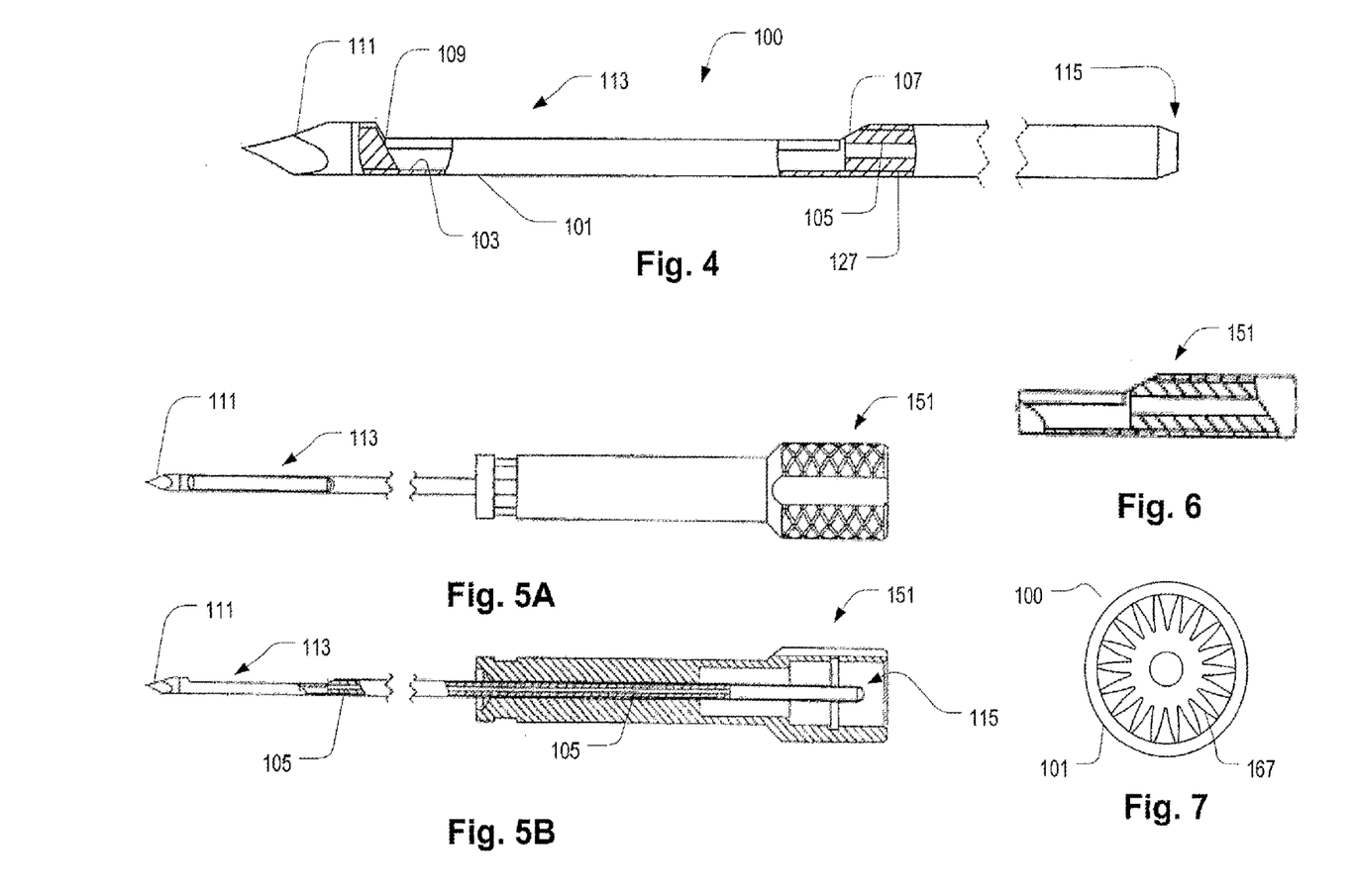
FIG. 4 illustrates a detail of a biopsy needle stylet and sample chamber at a distal end of the biopsy needle.
FIGS. 5A and 5B illustrate an assembly including the needle of FIG. 1
FIG. 6 illustrates a detail of the stylet near a proximal end of a sample chamber.
FIG. 7 illustrates an alternative reinforcement and tissue block.

A trocar 111 or other type of cutting tip may be proved at the distal end of the stylet. The beveled end 115 of the stylet 100 may be press-fitted into a hub 151. The beveled end 115, so-fitted, may extend into a recess portion 115 of the hub 151 to provide a portion of a connector. For example, the bevel may stretch a flexible annular adapter (not shown) to form a seal. An alternative insert 167 is shown in FIG. 7. The alternative insert 167 may be formed by extrusion, for example, and may be affixed to the stylet 100 wall 101 as discussed above.

Figure 8A:
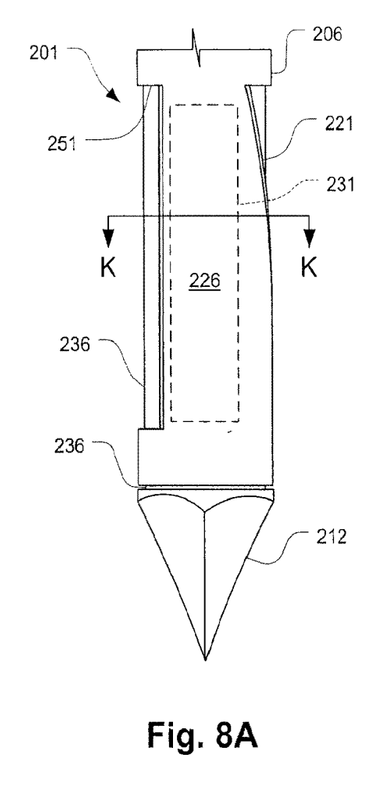
FIGS. 8A through 8F illustrate a type of cutting sheath and operational aspects.

Note that although in the above embodiments, the biopsy needle was described as being used with a cutting sheath that advances and rotates to cut a sample, it is possible to employ a rotating sheath with a blade that is parallel to the sheath axis, or nearly so. FIGS. 8A to 8F illustrate a biopsy needle 201 with an outer sheath 206. Referring to FIG. 8A, the outer sheath 206, in the present embodiment, is cylindrical and has an opening 251 with at least one sharp edge defining a blade 221. A cylinder-shaped inner sheath 236 has a port 231, which, in FIG. 8A, is aligned with the opening 251. The port 231 provides access to a sample chamber 226 which is defined by a volume within the inner sheath 236. A trocar 212 is affixed to a distal end of the inner sheath 236. A handle (not shown) is presumed to be provided, opposite the trocar 212, to support the biopsy needle 200. Note that the sample chamber 226 is not shown with the preferred dimensions as discussed above with reference to FIGS. 2A and 2B but is indicated figuratively here for purposes of discussing the cutting sheath operation.

Figure 8B:
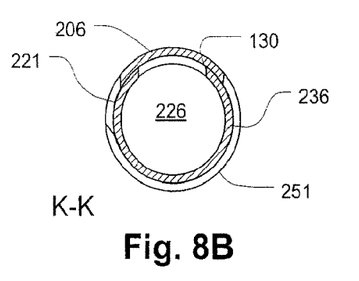

FIGS. 8B through 8F show, in section D-D, the needle 201 of FIG. 8A in successive stages of a sampling operation. These stages occur after the needle 201 is inserted into living tissue, a sample of which is to be excised for a biopsy. In FIG. 8B, the outer sheath 206 begins in a position in which it covers the port 231. The needle 201 is inserted while the outer sheath 206 is in this position relative to the inner sheath 236. Once the biopsy needle 201 is in position for sampling, the outer sheath 206 is rotated progressively in a counter-clockwise direction. The counter-clockwise rotation of the outer sheath 206 proceeds progressively through the stages indicated by FIGS. 8B through 8F. The outer sheath 206 may be driven by any suitable drive mechanism.

Figure 8C:
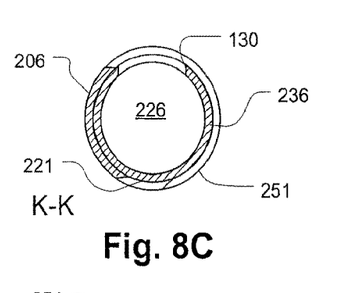
Figure 8D:
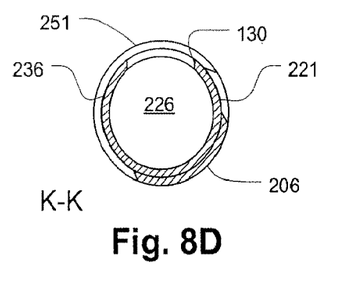

While the biopsy needle is in the insertion position shown in FIG. 8B, and after insertion into the tissue to be sampled (not shown), a vacuum is generated in the sample chamber 226 by drawing air through the inner sheath 236. The vacuum may be generated by any suitable device. Once a vacuum has been generated, the outer sheath 206 begins to rotate in the counter-clockwise direction. In FIG. 8C, the opening 251 is shown after having moved partly toward a position of coincidence with the port 231. As the rotation proceeds, the blade 221 advances toward the port 231. In this position, the vacuum, created in the sample chamber 226, draws tissue to be sampled through the opening 251 and port 231 until it begins to enter the sample chamber 226. The outer sheath 206, at this point, moves counter-clockwise toward the position shown in FIG. 8D where the port 231 is fully uncovered, the opening 251 having moved into coincidence with the opening 231. The vacuum causes tissue to be drawn into the sample chamber 226 and the outer sheath 206 continues rotating in the counter-clockwise direction to the position shown in FIG. 8E.

Figure 8E:
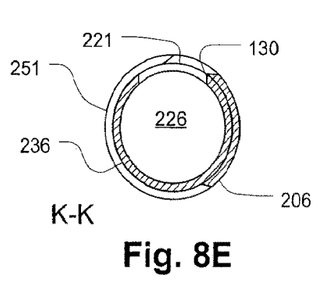
Figure 8F:
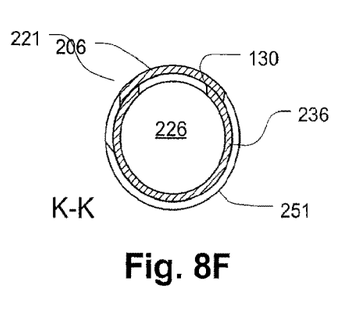

As the outer sheath 206 rotates toward the position shown in FIG. 8E, the blade 221 partly slices the tissue that has been drawn into the sample chamber 226. As the blade 221 continues toward the position of FIG. 8F, the tissue sample is completely severed from the host and held within the sample chamber 226 while a portion of the outer sheath 206 behind the blade 221 covers the port 231. The biopsy needle 201 can then be withdrawn from the inserted position as it retains the sample.

To remove the tissue sample, the operation depicted in FIGS. 8B through 8F may be repeated. However, in this case, a positive pressure may be generated in sample chamber 226 before starting the cycle. As the outer sheath 206 rotates clockwise through the successive positions starting with the one shown in FIG. 8F, a pressure is applied to the sample chamber 226 and the port 231 is uncovered. This causes the pressure in sample chamber 226 to force the tissue sample out through the uncovered port (about the position shown in FIG. 8D). The cycle may then continue to the point shown in FIG. 8B.

As in the previous embodiments, the outer sheath 206 could rotate in either direction, or both directions, in alternative embodiments. For example, the port 231 could be uncovered by rotating in one direction and the cutting operation and covering could occur after reversing the direction of rotation immediately after uncovering the port 231. This alternative may be provided for all of the embodiments described herein. In addition, the blade 221 may be on either or both sides of the opening 251. As in the previous embodiments, the speed of rotation of the outer sheath 206 may be constant or variable. For example, to reduce amplify torque from the drive mechanism, a reduced force/torque transmission ratio of the drive may be provided to level the prime mover load through the cutting phase. The port 231 may be angled to help reduce the instantaneous torque load on the outer sheath 206 drive mechanism (not shown).

Figure 9:
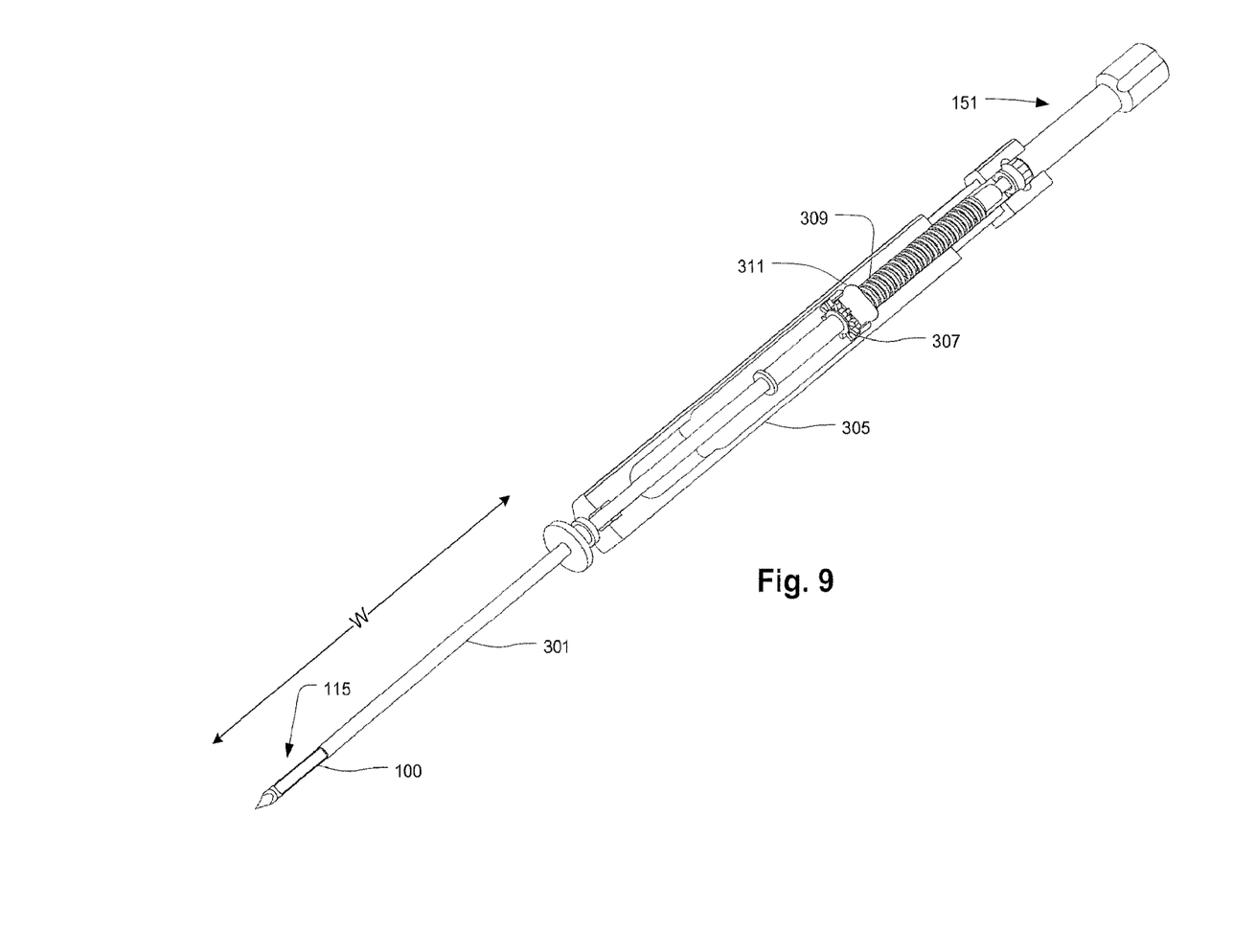
FIG. 9 shows a stylet and another type of cutting sheath in a modular consumable component that includes the stylet of the foregoing figures.

The other type of cutting sheath discussed above is illustrated in FIGS. 1B and 9. The stylet 100 lies within the cutting sheath 301 and both are held in a frame 305. The stylet 100 extends all the way to the hub 151 which is held in a single longitudinal position relative to the frame 305, thereby preventing the stylet 100 from moving axially. The cutting sheath 301 simultaneously rotates and advances and retracts relative to the frame 305 when a gear 307 is correspondingly driven rotationally by a drive, which is shown figuratively at 174 in FIG. 1B. The gear 307 is attached to the cutting sheath 301 and a threaded cylinder 309 in mesh with a nut 311 affixed to the frame 305. Thus, the rotation of the gear 307 causes axial translation of the cutting sheath 301 as well as rotation thereof. The device shown in FIG. 9 may form part of a disposable unit that fits into a reusable drive.

Figure 10:
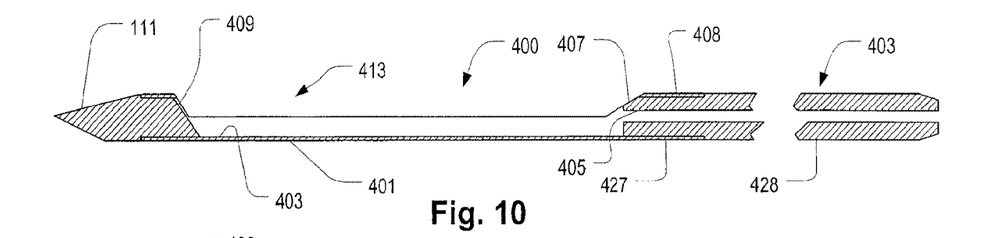
FIG. 10 shows a biopsy needle stylet with a single-piece reinforced section over the length that is proximal of the sample chamber.
Figure 11:
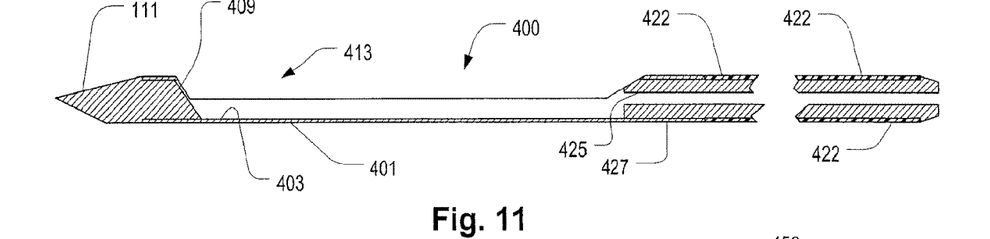
FIG. 11 shows a biopsy needle stylet with a composite reinforced section over the length that is proximal of the sample chamber.

Referring to FIG. 10, a biopsy needle stylet 400 is similar to the biopsy needle stylet of FIG. 4, having a sample chamber opening 413 with sloping edges 407 and 409 and an interior 403 formed from a cylindrical element 401. The proximal part 427 of the cylindrical element 401 receives an extension 408 of a heavy stylet portion 428. The thick-walled heavy stylet portion 428 provides an element which is substantially stiffer than a cylinder whose wall thickness and diameter is the same as that coinciding with the sample recess 412 such that this embodiment may avoid the need for an additional reinforcement. Other features are similar to the embodiment of FIG. 4. Referring to FIG. 11, in a further variation, the reinforcement is obtained in a main portion of the stylet 403 by means of a composite reinforcement element such as a carbon fiber wind layer 422. Here, the element 425 may be thinner-walled than in previous embodiments due to the additional stiffness provided by the composite support 422.

Figures 12A, 12B:
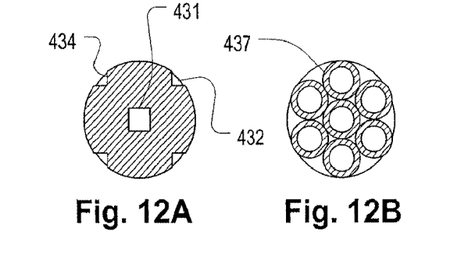
FIGS. 12A and 12B are illustrations for purposes of discussing various kinds of reinforcement components.

The internal reinforcement elements described in the foregoing can have various cross-sectional shapes, for example a cross-shape as indicated at 434, which may provide vacuum-transmitting lumens at the corners 432 or may include a central lumen 431 for that purpose. Other shapes such as triangular, square, pentagonal or lobed structures may be employed, again, with or without a centrally-located lumen.

Figure 13A:
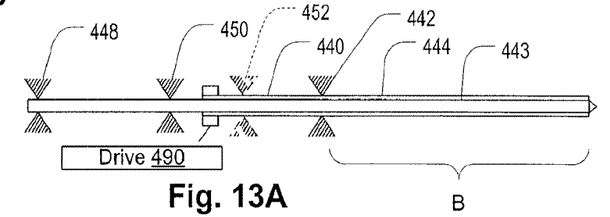
FIGS. 13A and 13B illustrate overconstraining of the stylet to reduce flexion in the needle.
Figure 13B:
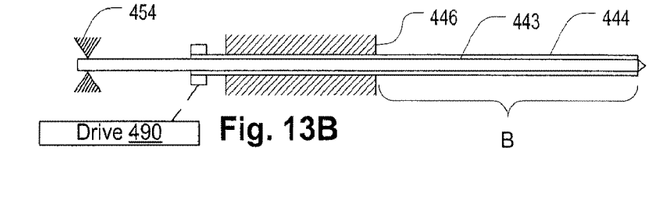

The issue of rigidity is also preferably addressed by means of a constraining support structure that helps to prevent the bending of the stylet. FIGS. 13A and 13B show stylet 443 with a working portion B and a supported portion proximal (remainder of the stylet 443 to the left in the drawings) thereof. Typically needles have a substantial length in the proximal part, which extends well into the body of the support, and control apparatus with which it interoperates. Support for the needle is typically provided by holding the needle at it rear end where it engages a support apparatus. For example, many biopsy needles have a needle shooting mode in which the needle is driven into, or adjacent, the tissue mass to be sampled by a spring or other paroxysmal actuator. So the proximal terminal end of the needle would ordinarily be held by such a component, which is illustrated figuratively as the support points 448 and 454 in both of FIGS. 13A and 13B. The distal support is indicated at 442 in FIG. 13A in a typical configuration. Support of the stylet 443 may be provided by a part of a permanent reusable structure, a part of a disposable, limited use structure, or a combination of the permanent reusable structure and the disposable structure. For example, see U.S. application Ser. No. 10/500,522 (published as U.S. 2005/0203439), now U.S. Pat. No. 8,109,885, and Ser. No. 10/500,518 (published as U.S. 2005/0165328), now U.S. Pat. No. 8,002,713, incorporated by reference above which show that the needle is carried by a plastic carrier that accompanies the non-reusable unit.

Preferably, additional or modified supports are provided as discussed below. Both embodiments of FIGS. 13A and 13B have a cutting sheath 444 driven by a drive 490, which can be either rotational or axial or both as discussed above and in the documents incorporated by reference. The cutting sheath tightly encloses the stylet 443 so that support of the cutting sheath 444 provides support of the stylet 443 therewithin. In the present embodiment, additional support is provided by the supports 450, which are approximately equidistant between supports 442 and 448. Additional supports or alternative locations for the additional support are indicated at 452. The result of the additional support is to constrain the ability of the stylet 443 and sheath 444 combination to bend.

The most effective location for the additional supports 450 is midway between the supports 440 and 448 but this may or may not be possible given other packaging requirements, depending on the particulars of the application. A compromise on the position of additional supports may therefore be required. Additional supports 452 and the strength and rigidity provided by the supports may be combined to aid in preventing bending. In addition or alternatively, as illustrated in embodiment of FIG. 13B, an elongate support 446 may be provided to constrain the bending of the stylet 443 and sheath 444 combination. The supports may be provided in the design of the biopsy needle in a variety of fashions. They may include collars, recesses in fixed bulkheads, protrusions in the housing, or any functional element that constrains movement and bending of the stylet 443 and sheath 444 combination. It has been found that for smaller diameter needles, such as a 14 gauge needle, that the additional constraint of the needle is important compensation for the thinness of the needle and has resulted in higher operational reliability than when the support is provided without significantly constraining bending. Preferably, at least a multiple of the supports 448, 452, 450, 442, or a major fraction of support 446 should coincide with the longitudinal extent of the reinforcement or nearly so, so that the fixity of the supports is transmitted through the reinforcement's rigidity, to the stylet.

To assist in securing large sample size, the magnitude of the vacuum used to draw samples into the sample chamber is preferably at least 21 in. Hg and more preferably at least 22 in. Hg.

While the present invention has been disclosed with reference to certain preferred exemplary embodiments, numerous modifications, alterations, and changes to the described exemplary embodiments are possible without departing from the sphere and scope of the present invention. Accordingly, it is intended that the present invention not be limited to the described exemplary embodiments, but that it have the full scope of the following claims and the equivalents thereof.

The invention claimed is:

1. A biopsy device, comprising:
a cylindrical hollow stylet having a proximal portion, and having a distal end portion with a closed distal end and a sample recess configured to define a side opening distal to the proximal portion to receive biopsy samples;
a mounting member configured to support the proximal portion of the cylindrical hollow stylet at multiple points such that bending of the proximal portion is resisted by the mounting member supporting the proximal portion at at least three discontinuous spaced support points, the cylindrical hollow stylet coincides with each of the at least three discontinuous spaced support points; and
a longitudinal reinforcement insert having a longitudinal length, the longitudinal reinforcement insert positioned within the cylindrical hollow stylet inside the proximal portion of the cylindrical hollow stylet and immovably connected to the cylindrical hollow stylet, the longitudinal reinforcement insert having an elongate channel that extends along the longitudinal length of the longitudinal reinforcement insert within the proximal portion of the cylindrical hollow stylet and is configured to maintain a fluid passageway through the cylindrical hollow stylet, the longitudinal reinforcement insert having a continuous extent portion along the longitudinal length that coincides with each of the at least three discontinuous spaced support points, such that the longitudinal reinforcement insert and the cylindrical hollow stylet resist bending, wherein the longitudinal reinforcement insert has a distal terminal end proximal to the side opening.

2. The biopsy device of claim 1, wherein the longitudinal reinforcement insert is immovably affixed at spaced positions to the cylindrical hollow stylet, and a portion of the longitudinal reinforcement insert internal to the cylindrical hollow stylet has a non-circular cross-sectional shape configured to effect the fluid passageway across the longitudinal reinforcement insert.

3. The biopsy device of claim 1, wherein the sample recess is a longitudinal opening in a side wall of the cylindrical hollow stylet, the longitudinal opening having longitudinally oriented cutting edges on lateral sides of the longitudinal opening, wherein each of the longitudinally oriented cutting edges has a height that is between 2.5 and 4 times a wall thickness of the side wall, the longitudinally oriented cutting edges define a pair of angled opposed inside surfaces, and each of the longitudinally oriented cutting edges define an apex angle measured from a respective inside surface of the pair of angled opposed inside surfaces of the longitudinally oriented cutting edges.

4. The biopsy device of claim 1, wherein the distal terminal end of the longitudinal reinforcement insert has a beveled surface; and wherein the beveled surface coincides with the sample recess.

5. A biopsy device, comprising:
a hollow stylet having a side wall and a distal end portion with a sample recess extending through the side wall to define a sample chamber, and a proximal end portion proximal to the sample recess, the distal end portion and the proximal end portion being disposed on a longitudinal axis;
a mounting structure configured to define at least three discontinuous longitudinally spaced support points, the hollow stylet simultaneously coinciding with each of the at least three discontinuous longitudinally spaced support points; and
a longitudinal reinforcement having a distal terminal end, the longitudinal reinforcement having at least one longitudinal channel along the longitudinal axis, the longitudinal reinforcement located at the proximal portion of the hollow stylet, the distal terminal end of the longitudinal reinforcement being proximal to the sample recess, the longitudinal reinforcement configured to maintain a fluid passageway through the hollow stylet via the at least one longitudinal channel, and the longitudinal reinforcement having a continuous extent portion configured to reinforce the hollow stylet at the at least three discontinuous longitudinally spaced support points of the mounting structure.

6. The biopsy device of claim 5, wherein one of the at least three discontinuous longitudinally spaced support points is included in an axially-elongated support element located at a distal end of the mounting structure.

7. The biopsy device of claim 5, wherein the hollow stylet has a first cross-sectional shape, and the longitudinal reinforcement is a longitudinal insert having a portion positioned internal to the hollow stylet, the portion having a second cross-sectional shape different from the first cross-sectional shape of the hollow stylet.

8. The biopsy device of claim 5, wherein the hollow stylet has a central lumen, the central lumen defining an inner surface, wherein the longitudinal reinforcement is a longitudinal insert having an outer surface, and the longitudinal insert is positioned in the central lumen at the proximal end portion of the hollow stylet, wherein the outer surface of the longitudinal insert is immovably affixed to the inner surface of the central lumen of the hollow stylet.

9. The biopsy device of claim 5, wherein the longitudinal reinforcement is a longitudinally continuous insert, the longitudinally continuous insert in its entirety being located within the proximal end portion of the hollow stylet and immovably affixed to the hollow stylet.

10. The biopsy device of claim 5, wherein a ratio of a diameter of the hollow stylet to a wall thickness of the hollow stylet is less than 15:1 and greater than 4:1.

11. The biopsy device of claim 5, wherein the hollow stylet has a working length that extends distally from the mounting structure.

12. The biopsy device of claim 5, wherein the sample recess is a longitudinal recess having cutting edges that extend parallel to the longitudinal axis on lateral sides of the longitudinal recess.

13. The biopsy device of claim 12, wherein the cutting edges have a depth, perpendicular to the longitudinal axis, of between 2.5 and 4 times a thickness of the side wall.

14. The biopsy device of claim 12, wherein each of the cutting edges has a height that is between 2.5 and 4 times a wall thickness of the side wall, the cutting edges define a pair of angled opposed inside surfaces, and each of the cutting edges define an apex angle measured from a respective inside surface of the pair of angled opposed inside surfaces of the cutting edges.

15. The biopsy device of claim 12, wherein a distance between the cutting edges is less than an outer diameter of the hollow stylet.

16. The biopsy device of claim 5, wherein the at least one longitudinal channel is a single longitudinal channel, the single longitudinal channel having a length that is the same as an entire length of the longitudinal reinforcement, and the single longitudinal channel located to pass through the longitudinal reinforcement along the entire length of the longitudinal reinforcement.

17. A biopsy device, comprising:
   a mounting structure configured to define at least three discontinuous longitudinally spaced support points;
   a hollow stylet having a lumen, a proximal portion, and a distal portion, the proximal portion having a proximal end, the distal portion having a side sample chamber opening configured to receive biopsy samples and a trocar tip distal to the side sample chamber opening, the hollow stylet having a fluid passageway between the proximal end and the side sample chamber opening, the proximal portion simultaneously coinciding with each of the at least three discontinuous spaced support points; and
   a longitudinal reinforcement insert located in the lumen at the proximal portion of the stylet, and the longitudinal reinforcement insert being immovably affixed to the proximal portion of the hollow stylet, the longitudinal reinforcement insert having a longitudinal length, the longitudinal reinforcement insert defining a longitudinal fluid path through the longitudinal length of the longitudinal reinforcement insert, the longitudinal fluid path configured to maintain the fluid passageway between the proximal end of the proximal portion of the hollow stylet and the side sample chamber opening of the distal portion of the hollow stylet, the longitudinal reinforcement insert configured to reinforce the proximal portion of the hollow stylet at the at least three discontinuous longitudinally spaced support points of the mounting structure, wherein the longitudinal reinforcement insert has a distal terminal end proximal to the side sample chamber opening.

18. The biopsy device of claim 17, wherein the side sample chamber opening is a longitudinal opening in a side wall of the hollow stylet, the longitudinal opening having longitudinally oriented cutting edges on lateral sides of the longitudinal opening, wherein each of the longitudinally oriented cutting edges has a height that is between 2.5 and 4 times a wall thickness of the side wall, the longitudinally oriented cutting edges define a pair of angled opposed inside surfaces, and each of the longitudinally oriented cutting edges define an apex angle measured from a respective inside surface of the pair of angled opposed inside surfaces of the longitudinally oriented cutting edges.

19. The biopsy device of claim 17, further comprising a vacuum pump coupled in fluid communication with the side sample chamber opening of the hollow stylet via the longitudinal reinforcement insert at the proximal portion of the hollow stylet.

20. A biopsy device, comprising:
   a hollow stylet having a single side wall and a distal end portion with a sample recess extending through the single side wall to define a sample chamber, and a proximal end portion proximal to the sample recess, the distal end portion and the proximal end portion being disposed on a longitudinal axis;
   a mounting structure configured to define at least three discontinuous longitudinally spaced support points, the hollow stylet simultaneously coinciding with each of the at least three discontinuous longitudinally spaced support points; and
   a longitudinal reinforcement having a length and a distal terminal end, the longitudinal reinforcement located inside the proximal portion of the hollow stylet with the distal terminal end being proximal to the sample recess of the hollow stylet, the longitudinal reinforcement being immovably connected to the single side wall of the hollow stylet and configured with an elongate passageway that extends along an entirety of the length of the longitudinal reinforcement to maintain a fluid passageway through the hollow stylet, the longitudinal reinforcement configured to reinforce the hollow stylet and simultaneously coincide with each of the at least three discontinuous longitudinally spaced support points of the mounting structure, such that the hollow stylet resists bending.

21. The biopsy device of claim 20, wherein the sample recess is a longitudinal recess having cutting edges that extend parallel to the longitudinal axis on lateral sides of the longitudinal recess, wherein the cutting edges define an apex angle of about 40°.

22. The biopsy device of claim 20, further comprising a cutting cannula, the hollow stylet being received in the cutting cannula, the cutting cannula being movable relative to the hollow stylet.

\* \* \* \* \*